United States Patent [19]

Lomoelder et al.

[11] Patent Number: 5,459,204

[45] Date of Patent: Oct. 17, 1995

[54] ISOPHORONE URETHANE POLYAMINE, A PROCESS FOR ITS PREPARATION AND ITS USE

[75] Inventors: Rainer Lomoelder, Muenster; Wilfried Paulen, Recklinghausen; Felix Schmitt, Herten; Elmar Wolf, Recklinghausen, all of Germany

[73] Assignee: Huels Aktiengesellschaft, Marl, Germany

[21] Appl. No.: 206,854

[22] Filed: Mar. 7, 1994

[30] Foreign Application Priority Data

Apr. 10, 1993 [DE] Germany .................. 43 11 922.0

[51] Int. Cl.$^6$ .............. C07C 271/34; C07C 271/36; C08G 18/10; C08G 18/32
[52] U.S. Cl. .............. 525/409; 525/452; 525/453; 525/460; 528/60; 528/61; 528/62; 528/64; 528/111; 528/118; 528/122; 560/25; 560/115; 560/158; 544/222
[58] Field of Search .............. 544/223; 560/25, 560/115, 158; 528/60, 61, 62, 64, 111, 118, 122; 525/452, 453, 460, 409

[56] References Cited

U.S. PATENT DOCUMENTS

| | | | |
|---|---|---|---|
| 3,352,913 | 11/1967 | Schmitt et al. | 260/563 |
| 3,941,753 | 3/1976 | Brinkmann et al. | 528/59 |
| 4,108,842 | 8/1978 | Konig et al. | 528/61 |
| 4,224,417 | 9/1980 | Hajek et al. | 521/166 |

FOREIGN PATENT DOCUMENTS

| | | |
|---|---|---|
| 2328006 | 5/1977 | France . |
| 2362171 | 3/1978 | France . |

*Primary Examiner*—Frederick Krass
*Attorney, Agent, or Firm*—Oblon, Spivak, McClelland, Maier & Neustadt

[57] ABSTRACT

The invention relates to a new polyamine of the following composition:

(I)

wherein $1 \geq n \geq 6$,
R represents the hydrocarbon radical of a (cyclo)aliphatic, araliphatic or aromatic diisocyanate having 6–20 C atoms or a trimer thereof and
wherein when $2 \geq n \geq 6$,
$R^1$ represents an n-valent organic radical such as is formed by removal of n OH groups from a polyhydroxy compound which optionally contains ether oxygen atoms and has an average molecular weight Mn of between 60 and 5,000; and
when $n=1$,
$R^1$ represents It furthermore relates to a process for the preparation of a polyamine, in which certain diisocyanates, adducts of diisocyanates with polyols or trimers thereof are reacted with the Schiff base of the following composition:

wherein $R^2$=H or a branched or unbranched $C_{1-14}$-alkyl radical and $R^3$=a branched or unbranched $C_{1-14}$-alkyl radical, an $C_{1-14}$ alkyl-substituted phenyl radical or a $C_1$–$C_8$-cycloalkyl radical and, when the reaction has taken place, the polyazomethine formed (poly-Schiff base) is hydrolyzed completely with excess water and the carbonyl compound formed is distilled off.

The polyamine according to the invention is employed for curing epoxy resins.

9 Claims, No Drawings

ISOPHORONE URETHANE POLYAMINE, A PROCESS FOR ITS PREPARATION AND ITS USE

This application claims the benefit of priority under 35 U.S.C. 119 to DE P43 11 922.0 filed in Germany Apr. 10, 1993, the entire contents of which are hereby incorporated by reference.

BACKGROUND OF THE INVENTION

1. Field of the Invention

The present invention relates to a new polyamine, a process for its preparation and its use as epoxy resin hardener.

2. Discussion of the Background

Polyamines, especially diamines, on the one hand have acquired prominent importance as starting components for the preparation of polyamides, and on the other hand are widely employed for curing epoxy resins especially those based on bisphenol A.

While low molecular weight polyamines are readily accessible industrially and a large selection is therefore available, the problem of preparation of higher molecular weight di- and polyamines has not yet been solved satisfactorily.

A process which has been known for a long time for the preparation of such tailor-made polyamines comprises reacting NCO prepolymers with amino alcohols, the $NH_2$ group of which is protected from the NCO group in the form of an aldimine or ketimine group, and then hydrolyzing the product. In this process, it is important for the amino group to be separated from the OH group by at least 6 C atoms, since if the two groups are closer together, 5-, 6- and 7-membered rings can be formed and the desired Schiff base are obtained only as a byproduct. It has therefore not been possible to date, for amino alcohols in which the functional groups are 2–4 C atoms apart to be employed for the preparation of polyamines.

The object of the present invention was therefore to provide a simple, reproducible process for the preparation of higher molecular weight di- and polyamines.

Surprisingly, it has been found in parallel that certain amino alcohols, in which the functional groups are separated from one another by 4 C atoms, do not give a heterocyclic 7-membered ring with aldehydes and ketones, as expected, but give azomethines (Schiff bases) if the amino alcohol is the compound 3-aminomethyl-3,5,5-trimethyl cyclohexanol:

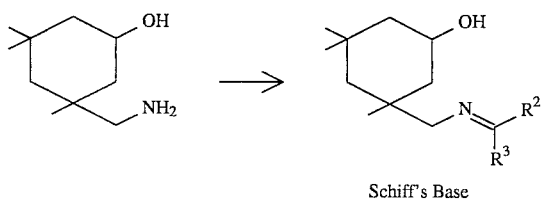

Schiff's Base

A separate Application DE P 43 11 901.8 of the same priority relates to these Schiff bases.

In achieving the object, it has been possible to prepare high molecular weight di- and polyamines in a simple manner by reaction of the above Schiff base and diisocyanate prepolymers (adducts of diisocyanates with polyols or trimers of diisocyanates) and subsequent hydrolysis.

SUMMARY OF THE INVENTION

The invention therefore relates to polyamines having the following composition:

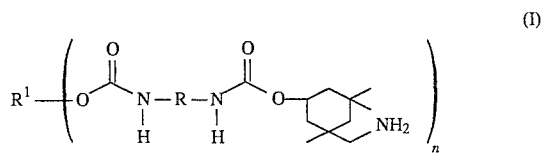

(I)

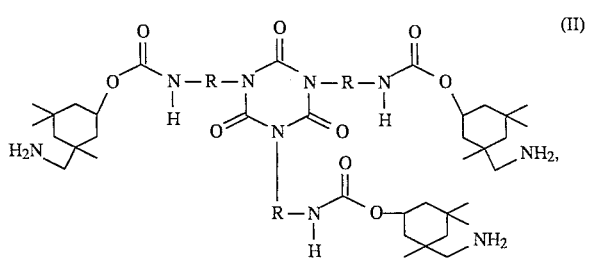

(II)

wherein $1 \leq n \leq 6$,

R represents the hydrocarbon radical of a (cyclo)aliphatic, araliphatic or aromatic diisocyanate having 6–20 C atoms or trimers thereof; and wherein when $2 \leq n \leq 6$, $R^1$ represents an n-valent organic radical such as is formed by removal of n OH groups from a polyhydroxy compound which optionally contains ether oxygen atoms and has an average molecular weight Mn of between 60 and 5,000, or when n=1, $R^1$ represents

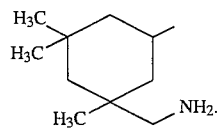

A second object of the present invention relates to a process for the preparation of the polyamines of formula (I) and (II), comprising:

i) reacting a diisocyanate, an adduct of a diisocyanate with a polyol (Ia) or a trimer thereof (IIa)

OCN—R—NCO

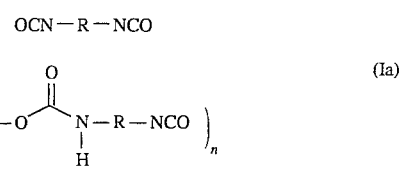

(Ia)

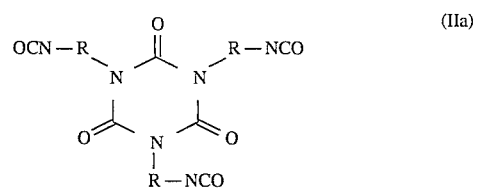

(IIa)

wherein n, R and $R^1$ have the above-identified meaning with the Schiff base of the following composition:

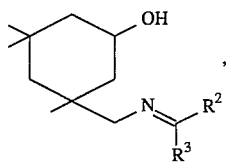

wherein $R^2$=H or a branched or unbranched $C_{1-14}$-alkyl radical and $R^3$=a branched or unbranched $C_{1-14}$-alkyl radical, an $C_{1-14}$ alkyl-substituted phenyl radical or a $C_1$-$C_8$-cycloalkyl radical, in an NCO:OH equivalence ratio of 1:1 to form resulting polyazomethines (poly-Schiff bases) of the formula Ib and IIb

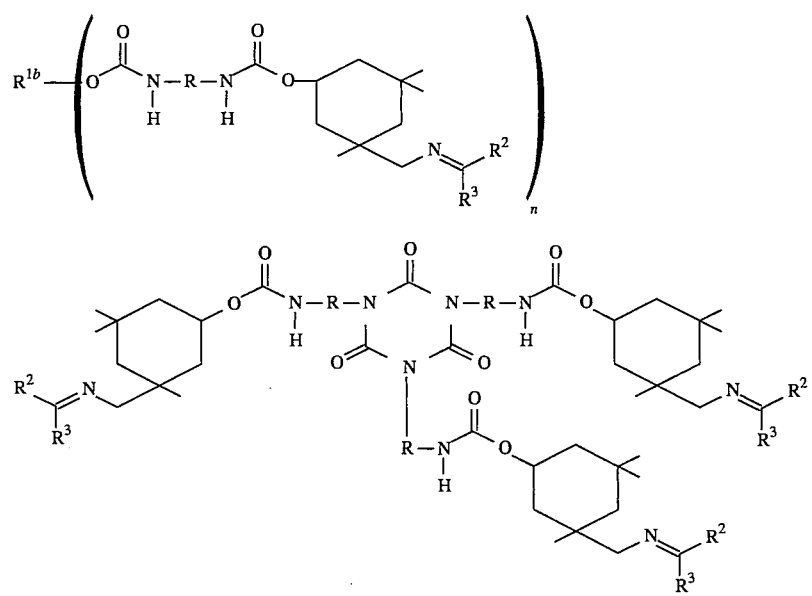

wherein when $2 \leq n \leq 6$, $R^{1b}$ represents an n-valent organic radical such as is formed by removal of n OH groups from a polyhydroxy compound which optionally contains ether oxygen atoms and has an average molecular weight Mn of between 60 and 5,000, or when n=1, $R^{1b}$ represents

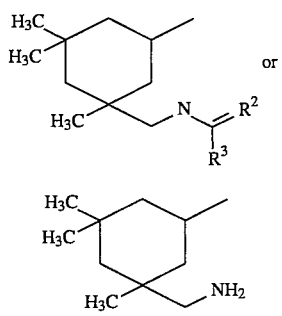

ii) hydrolyzing the azomethine groups with excess water; and iii) distilling off the carbonyl compound formed.

A third object of the present invention relates to a method of curing an epoxy resin with a polyamine.

A fourth object of the present invention relates to an epoxy resin system comprising an epoxy resin component and a polyamine component.

The objects of the present invention is provided by the above-identified polyamines of formula (I) and (II).

The polyamine of formula (I) and (II) are useful as a curing agent for epoxy resins and as a starting component for the preparation of polyamides.

DETAILED DESCRIPTION OF THE PREFERRED EMBODIMENTS

The polyamine according to the invention is distinguished by a molecular weight Mn of 500–6,000 and a basic amine content of 0.3–4 mmol of $NH_2$/g. Their consistency can be varied within a wide range. While the polyamines according to the invention containing ether groups have a viscosity of 50,000–$10^6$ mPa.s, the polyamines containing isocyanurate groups are high-melting compounds having a melting point >150° C.

According to the polyamine of formula (I), when $2 \leq n \leq 6$, the group $R^1$ is an n-valent organic radical. A suitable example is the organic radical formed by removing n hydroxy groups from a polyhydroxy compound which optionally contains ether oxygen atoms. Suitable polyhydroxy compounds include ethylene glycol, glycerol, hexanediol, di- and triethylene glycol, neopentylglycol, trimethylolpropane, octadecanediol, pentaerythritol, sorbitol, mannitol, maltitol and glycosides.

Preparation of polyamines:

The reaction between the NCO prepolymer or diisocyanate and the Schiff base depends on the state of aggregation of the diisocyanate or NCO prepolymer used. The reaction can be carried out without solvent or in aprotic solvents at temperatures of from 20° to 80° C.

In the case of low-viscosity NCO prepolymers, solvent can be omitted; in the case highly viscous and solid NCO prepolymers, however, solvent must be used. Possible solvents are, in principle, all those which contain no functional groups which react with NCO groups. Solvents which have proven particularly suitable ketones, such as acetone, methyl ethyl ketone, and aromatic hydrocarbons, such as toluene.

Preparation of isocyanate prepolymer:

The isocyanate prepolymers (Ia; IIa) used for the process of the invention are prepared according to methods known per se by reaction of polyhydroxy compounds with diisocyanates or by trimerization of diisocyanates.

The isocyanate prepolymers (Ia, IIa) employed for the process according to the invention can be prepared by conventional methods which are known per se. More specifically they can be prepared by reaction of polyhydroxy compounds with diisocyanates or by trimerization of diisocyanates.

Suitable polyhydroxy compounds are polyols having a molecular weight of 60–600, such as, for example, ethylene glycol, hexanediol, di- and triethylene glycol, neopentylglycol, trimethylolpropane, octadecanediol and $C_{36}$-diol. Polyether-polyols having a molecular weight Mn of 200–5,000 and 2–5, preferably 2–3 hydroxyl groups are preferably suitable. The polyethers containing hydroxyl groups which are possible according to the invention are those of the type which are known per se and are prepared by conventional methods. For example, suitable polyethers may be prepared by polymerization of epoxides, such as ethylene oxide, propylene oxide, tetrahydrofuran or styrene oxide, with themselves, for example in the presence of Lewis acids such as, for example, $BF_3$, or by addition of these epoxides, if appropriate as a mixture or in succession, onto initiator components containing reactive hydrogen atoms, such as water, alcohols and amines. Polybutadienes containing OH groups furthermore are employed for the isocyanate prepolymers.

Suitable starting components for the preparation of the isocyanate prepolymers (Ia) required for the process according to the invention are (cyclo)aliphatic, araliphatic and aromatic diisocyanates, such as are described, for example, by W. Siefken in *Justus Leibigs Annalen der Chemie*, 562, pages 75–136. Suitable examples include hexamethylene 1,6-diisocyanate, 2-methylpentamethylene diisocyanate, dodecane 1,12-diisocyanate, isophorone diisocyanate, tetramethylxylene diisocyanate, tolylene 2,4- and 2,6-diisocyanate and diphenylmethane 2,4'- and/or 4,4'-diisocyanate.

The isocyanate prepolymers (Ia) are prepared by conventional means in a manner such that 2 NCO equivalents of the diisocyanate per 1 OH equivalent of the polyol are reacted with one another in a known manner. The isocyanate prepolymers thus prepared still contain about 2–8% wt of free diisocyanate, depending on the molecular weight. In some cases, it has proved to be expedient to employ isocyanate prepolymers having a monomer content of <0.5% wt for the process according to the invention. Such low-monomer isocyanate prepolymers are prepared in a manner such that a diisocyanate is reacted in a large excess with the polyol in a 1st stage, and in a 2nd stage, the unreacted diisocyanate is separated off from the reaction product by thin film distillation. The isocyanate prepolymers thus prepared contain <0.5% wt of diisocyanate, regardless of their molecular weight.

The isocyanate prepolymers IIa employed for the process according to the invention are prepared by conventional means in a known manner by trimerization of the diisocyanates already mentioned for the preparation of the isocyanate prepolymers Ia, as described, for example, in DE-C 26 44 684 and DE-C 29 16 201.

Preparation of Schiff base:

The following Schiff base is employed as a reaction component for the isocyanate prepolymers (Ia, IIa) in the process according to the invention:

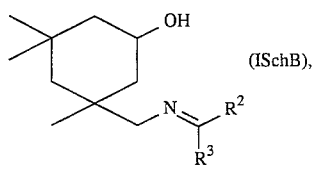

(ISchB),

The preparation of the Schiff base can be carried out either in solution or without solvent.

When the reaction is carried out in solution, toluene or xylene is preferred as (inert) solvent. The azomethine formation can be accelerated by addition of 0.01–0.1% by weight of acid such as $H_3PO_4$. This is advantageous when sluggishly reacting components are used, as is the case with sterically hindered amines and ketones. IPAA and toluene are mixed at room temperature and admixed with an equimolar amount of the carbonyl compound. The concentration of toluene is from about 50 to 80% by weight. The solution is then slowly heated to reflux and heated further with a water separator attached until the calculated amount of $H_2O$ has been distilled off. The toluene is then distilled off in vacuo. The concentration of the Schiff base so prepared is ≧99% (% by area in the gas chromatogram). In general, this purity is sufficient for further reaction of the Schiff base with NCO prepolymers to form poly-Schiff bases.

In the preparation without solvent, equimolar amounts of IPAA and the carbonyl component are mixed at room temperature and slowly heated to reflux and heated further until the calculated amount of $H_2O$ has been distilled off. It has proven advantageous to add the carbonyl component in an excess of from 10 to 30 wt. %. After the distillative separation of the water of reaction and the excess carbonyl component, vacuum is applied for a short time. The product of the process, thus prepared, according to the invention, has a purity of ≧99% and generally needs no further purification.

As the carbonyl component, in principle, all aldehydes and ketones are suitable for blocking the $NH_2$ function, provided that the carbonyl compound is capable of forming an azomethine group with the primary amine. Blocking agents which have proved to be particularly suitable are for example, from the aldehydes: acetaldehyde propionaldehyde, n-butyraldehyde and i-butyraldehyde, and from the ketones: methyl ethyl ketone, methyl n-propyl ketone, diethyl ketone, methyl isobutyl ketone and diisobutyl ketone.

When the reaction of the isocyanate prepolymers (Ia, IIa) with the Schiff base (I) has been carried out, the reaction mixture of the 1st stage is now hydrolyzed in a 2nd process step:

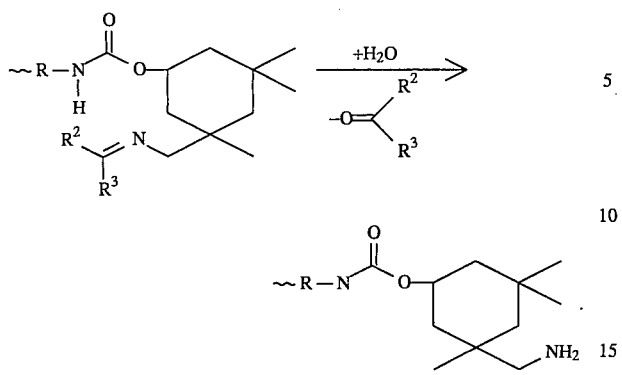

The carbonyl compounds are split off in a manner such that the blocked polyamine, if appropriate in the presence of 0.1–0.5% of emulsifiers, is heated with excess $H_2O$ (2–3 times the molar amount of the blocked polyamine) while stirring intensively, $H_2O$, the carbonyl compound liberated and, if appropriate, the solvent being distilled off simultaneously under atmospheric pressure.

After removing the last residues of $H_2O$, the polyamine is further heated in vacuo at 100°–140° C. for about 2–4 hours. The polyamines thus prepared no longer contain azomethine groups; rather exclusively primary NH2 groups are present. The $H_2O$ content is 0.1–0.6% wt.

The present invention furthermore relates to a method of curing epoxy resins using the compounds according to the invention.

Suitable epoxy resins are in principle all those which contain ≧2 epoxide groups per molecule; the epoxy resins based on bisphenol A and F have proved to be particularly suitable.

Since the polyamines according to the invention are highly viscous or solid substances, they are as a rule employed in solvent-containing form. Suitable solvents are, for example benzyl alcohol, nonylphenol, toluene, xylene and N-methylpyrrolidone.

The polyamines according to the invention can be reacted with the epoxy resin either by themselves or in combination with a diamine or primary monoamine, if appropriate in the presence of known catalysts, such as 2,4,6-trisdimethylaminomethylphenol, salicylic acid or dimethylbenzylamine. By suitable choice of the combination of components: polyamine, diamine and monoamine, coatings having good mechanical properties and of any desired flexibility can be produced at room temperature (with a constant EP resin).

Suitable diamines which can be employed with the polyamines according to the invention are, for example, the following: ethylenediamine, 1,2-(1,3)-diaminopropane, 1,3-(1,4)-diaminobutane, 3-(isopropylamino)propylamine, 1-cyclohexylamino-3-aminopropane, 1,4-diaminocyclohexane, 1,3-diaminocyclohexane, isophoronediamine, 2-methylpentamethylenediamine, 2,2,4(2,4,4)-trimethylhexamethylenediamine, hexamethylenediamine, N-aminoethylpiperazine and m-xylylenediamine. Suitable monoamines which can be employed with the polyamines according to the invention and if appropriate with the diamines mentioned for preparation of the coatings according to the invention are: decylamine, dodecylamine, tridecylamine, butoxypropylamine, hexyloxypropylamine, 3-(2-ethylhexyloxy)propylamine, lauryloxypropylamine and diethylaminopropylamine.

Having generally described this invention, a further understanding can be obtained by reference to certain specific examples which are provided herein for purposes of illustration only and are not intended to be limiting unless otherwise specified.

A. Preparation of the Schiff base

A mixture of 342 parts by weight of 3-aminomethyl-3,5,5-trimethylcyclohexanol and 260 parts by weight of methyl isobutyl ketone is boiled under reflux, using a water separator, until 36 parts by weight of water have been separated off. The excess MIBK is then distilled off under reduced pressure. As a rule, further purification can be omitted. The OH number of the reaction product is 221 mg of KOH/g.

B. Preparation of the polyamines according to the invention

Example B1

254 parts by weight of Schiff base A and 560 parts by weight of an NCO prepolymer which has been prepared by known processes from 444 parts by weight of IPDI and 650 parts by weight of a polytetrahydrofurandiol with an average molecular weight of 650 are heated together at 50° C. until no further NCO can be detected (about 20 hours). 2,000 parts by weight of $H_2O$ are added to this poly-Schiff base and the mixture is heated at the boiling point, while stirring vigorously, the $H_2O$ being distilled off continuously under atmospheric pressure. When the reaction under atmospheric pressure has ended, the mixture is further heated at 100° C. under 0.1 torr for about another 4 hours in order to bring the reaction to completion.

The reaction product thus obtained contains exclusively primary amino groups. The azomethine group can no longer be detected by NMR measurement. The basis amine content is 1.3 mmol/g; the viscosity at 25° C. is $1.2 \times 10^6$ mPa.s. The $H_2O$ content is 0.3% wt.

Example B2

254 parts by weight of Schiff base A and 737 parts by weight of an NCO prepolymer which has been prepared by known processes from 444 parts by weight of IPDI and 1,000 parts by weight of a polytetrahydrofurandiol with an average molecular weight of 1,000 are reacted analogously to Example B1 and the product is then hydrolyzed with 2,500 parts by weight of $H_2O$ under the reaction conditions described in Example B1.

The reaction product has a content of basic amine of 1.05 mmol of $NH_2$/g and a viscosity of $10^6$ mPa.s (at 25° C.). The $H_2O$ content is 0.5% wt.

Example B3

254 parts by weight of Schiff base A and 1,313 parts by weight of an isocyanate prepolymer which has been prepared by known processes from 444 parts by weight of IPDI and 2,000 parts by weight of a bifunctional polypropylene glycol with an average molecular weight Mn of 2,000 are reacted analogously to Example B1 and the product is then hydrolyzed with 3,000 parts by weight of $H_2O$ under the reaction conditions described in Example B1.

The reaction product has a content of basic amine of 0.6 mmol of $NH_2$/g and a viscosity of $1.6 \times 10^5$ mPa.s (at 25° C.). The $H_2O$ content is 0.4% wt.

Example B4

244 parts by weight of trimeric IPDI containing 17.2% of NCO (VESTANAT T 1890, commercial product from Hüls AG) are dissolved in 300 parts by weight of acetone and reacted with 254 parts by weight of Schiff base A analogously to Example B1, and the product is then hydrolyzed with 1,500 parts by weight of $H_2O$ under the reaction conditions described in Example B1.

The reaction product has a content of basis amine of 1.4 mmol of $NH_2$/g and a melting range of 180°–190° C.; the $H_2O$ content is 0.2% wt.

C. Production of flexible epoxy resin coatings

I. Composition of the hardeners

Hardener 1:

80 parts by weight of polyamine B. 3, 20 parts by weight of benzyl alcohol and 15.7 parts by weight of IPD are mixed NH-active equivalent weight: 250

Viscosity (at 23° C.) mPa.s: 5990

Hardener 2:

80 parts by weight of polyamine B. 3, 20 parts by weight of benzyl alcohol and 45.9 parts by weight of 2-ethyl-hexyloxypropylamine are mixed NH-active equivalent weight: 250

Viscosity (at 23° C.) mPa.s: 437

Hardener 3:

70 parts by weight of polyamine B. 1, 30 parts by weight of benzyl alcohol and 11.4 parts by weight of IPD are mixed NH-active equivalent weight: 250

Viscosity (at 23° C.) mPa.: $10.8 \times 10^3$

Hardener 4:

70 parts by weight of polyamine B. 1, 30 parts by weight of benzyl alcohol and 33.6 parts by weight of 2-ethyl-hexyloxypropylamine are mixed NH-active equivalent weight: 250

Viscosity (at 23° C.) mPa.s: $1.33 \times 10^3$

C. II Curing of EPIKOTE® 828 with the hardeners according to the invention (epoxy:NH = 1:1); 7 days, room temperature

| Hardener comp. Parts by weight | | Tensile strength Nmm² (DIN 53 504) | Tensile elongation % (DIN 53 504) | Tear strength Nmm² (DIN 53 504) | Elongation at break % | Tear propagation resistance Nmm² (DIN 53 515) | Shore D |
|---|---|---|---|---|---|---|---|
| Hardener 1 | Hardener 2 | | | | | | |
| 80 | 20 | 19.4 ± 0.8 | 118.7 ± 17.7 | 19.4 ± 0.8 | 118.9 ± 17.3 | 50.4 ± 3.9 | 60 |
| 50 | 50 | 15.7 ± 0.7 | 174.7 ± 11.3 | 15.7 ± 0.7 | 174.7 ± 11.3 | 53.7 ± 2.5 | 55 |
| 25 | 75 | 11.6 ± 0.4 | 276.8 ± 8.9 | 11.6 ± 0.4 | 276.8 ± 8.9 | 33.0 ± 1.9 | 39 |
| 20 | 80 | 10.1 ± 0.2 | 277.4 ± 6.2 | 10.1 ± 0.2 | 277.5 ± 6.1 | 36.0 ± 1.2 | 37 |
| Hardener 3 | Hardener 4 | | | | | | Shore A |
| 100 | — | 25.7 ± 0.9 | 15.6 ± 1.4 | 21.8 ± 0.3 | 38 ± 2.5 | 73.7 ± 9.2 | — 70 |
| 75 | 25 | 17.5 ± 0.9 | 113.3 ± 9.2 | 17.5 ± 0.9 | 113.3 ± 9.2 | 50.2 ± 1.8 | — 63 |
| 50 | 50 | 14.6 ± 1.1 | 212.1 ± 1.1 | 14.6 ± 1.1 | 212.1 ± 12.5 | 45.8 ± 3.9 | — 45 |
| 25 | 75 | 14.6 ± 1.1 | 327.5 ± 12.5 | 9.3 ± 0.5 | 327.5 ± 12.5 | 30.7 ± 1.8 | 85 35 |
| — | 100 | 1.0 ± 0 | 185.9 ± 7.8 | 1.0 ± 0 | 186.3 ± 7.6 | 16.2 ± 2.8 | 61 — |

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A polyamine of the formula:

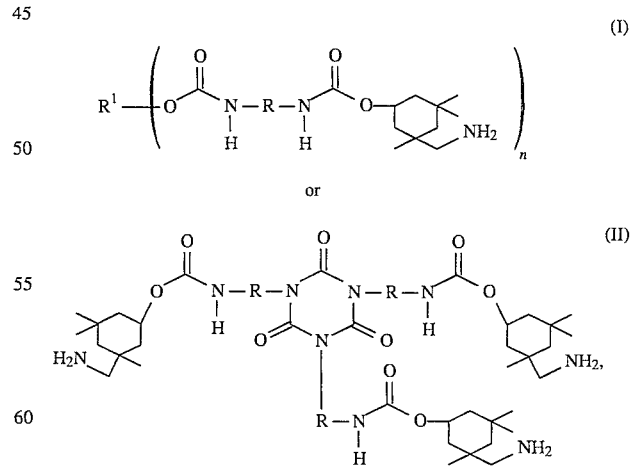

wherein $1 \leq n \leq 6$,

R represents the hydrocarbon radical of a (cyclo)aliphatic, araliphatic or aromatic diisocyanate having 6–20 C atoms or a trimer thereof; and wherein when $2 \leq n \leq 6$, $R^1$ represents an n-valent organic radical and has an average molecular weight Mn of between 60 and 5,000, and
when n=1,
$R^1$ represents

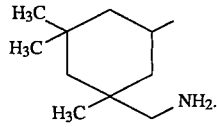

2. The polyamine of claim 1, wherein when $2 \leq n \leq 6$, $R^1$ is an n-valent organic radical formed by removal of n OH groups from a polyhydroxy compound.

3. The polyamine of claim 1, wherein when $2 \leq n \leq 6$, $R^1$ is an n-valent organic radical formed by removal of n OH groups from a polyhydroxy compound which contains ether oxygen atoms.

4. The polyamine of claim 1, wherein said polyamine has an average molecular weight Mn of 500–6,000.

5. The polyamine of claim 1, wherein said polyamine has a basic amine content of 0.3–4 mmol of $NH_2$/g.

6. The polyamine of claim 1, wherein said polyamine contains an isocyanurate group and has a melting point >150° C.

7. The polyamine of claim 1 wherein when $2 \leq n \leq 6$, $R^1$ is the organic radical formed by removing n hydroxy groups from a polyhydroxy compound selected from the group consisting of ethylene glycol, glycerol, hexanediol, di- and triethylene glycol, neopentylglycol, trimethylolpropane, octadecanediol, pentaerythritol, sorbitol, mannitol, maltitol, glycosides and a mixture thereof.

8. A method for curing epoxy resins comprising reacting an epoxy resin with the polyamine of claim 1.

9. An epoxy resin system comprising:
A) a first portion comprising an epoxy resin; and
B) a second portion comprising the polyamine of claim 1.

* * * * *